United States Patent [19]

Haralampu et al.

[11] Patent Number: 5,182,130
[45] Date of Patent: Jan. 26, 1993

[54] METHOD FOR PRODUCING AN EDIBLE PROLAMINE COATING FROM AN AQUEOUS LATEX

[75] Inventors: Stephen G. Haralampu, Plymouth; Stephen Sands, Wellesley; Akiva Gross, Newton, all of Mass.

[73] Assignee: Opta Food Ingredients, Inc., Cambridge, Mass.

[21] Appl. No.: 717,174

[22] Filed: Jun. 17, 1991

Related U.S. Application Data

[63] Continuation of Ser. No. 432,988, Nov. 6, 1989, abandoned.

[51] Int. Cl.$^5$ .............................................. A61K 9/38
[52] U.S. Cl. ...................................... 427/3; 424/477; 426/310; 427/212
[58] Field of Search .................... 427/3, 212, 384; 424/477, 491; 426/302, 305, 310

[56] References Cited

U.S. PATENT DOCUMENTS

| | | | |
|---|---|---|---|
| 3,840,676 | 10/1974 | Yamamoto et al. | 426/89 |
| 4,224,219 | 9/1980 | Van Blanton et al. | 106/149 |
| 4,543,370 | 9/1985 | Porter et al. | 424/440 |
| 4,876,094 | 10/1989 | Benton et al. | 426/472 |
| 4,876,097 | 10/1989 | Autant et al. | 426/656 |
| 5,021,248 | 6/1991 | Stark et al. | 426/531 |

FOREIGN PATENT DOCUMENTS

| | | |
|---|---|---|
| 1323056 | 2/1963 | France ............................. 424/477 |
| WO80/00659 | 4/1980 | PCT Int'l Appl. |
| WO89/05589 | 6/1989 | PCT Int'l Appl. |
| WO90/03123 | 4/1990 | PCT Int'l Appl. |

OTHER PUBLICATIONS

The New Encyclopaedia Britannica, vol. 5, Encyclopaedia Britannica, Inc., Chicago (1986) p. 165.

*Primary Examiner*—Shrive Beck
*Assistant Examiner*—Terry J. Owens
*Attorney, Agent, or Firm*—Hamilton, Brook, Smith & Reynolds

[57] ABSTRACT

A continuous edible coating or barrier is formed on a substrate by applying to the substrate a water-based prolamine latex which is substantially free of organic solvent. Additives to the latex may be used to modify the properties of the coating or barrier.

12 Claims, 2 Drawing Sheets

METHOD FOR PRODUCING AN EDIBLE PROLAMINE COATING FROM AN AQUEOUS LATEX

This is a continuation of co-pending application Ser. No. 07/432,988 filed on Nov. 6, 1989, now abandoned.

BACKGROUND

Edible coatings are used in foods to minimize the migration of components within the food system or between the food and its surrounding environment. For example such coatings prevent the diffusion of water, fats and/or oxygen into, out of, or within the food system. Of these, reducing moisture migration is the most important requirement in most cases. A change in either direction of moisture levels or water activity does not have to be very large to be very detrimental for the food quality. Moisture loss or uptake in a food can have dramatic effects on the texture, stability or yield of the food product. Moisture uptake can reduce or eliminate crispness, can speed enzymatic or chemical deterioration of flavors or nutrients, and can impair the food's structural integrity.

Edible barriers can also reduce gas permeability in foods. Oxygen uptake by a food often results in deleterious reactions which affect its flavor, nutritional quality and acceptability. In complex food systems, the migration of water or lipids within the food itself may have a detrimental effect on the perceived quality. Also, in processing operations, such as deep fat frying, coatings may reduce the migration of a processing aid, i.e., fat, into the food. In addition, barriers may be used to minimize the migration or loss of other additives, such as colors, flavors, preservatives, antioxidants, etc. . . Edible coatings also can be used to impart structural integrity to the surface of a food, making it less susceptible to mechanical damage.

Kester and Fennema ("Edible Films and Coatings: a Review," *Food Technology*, (1986), 40(12):47-59) reviewed the use of edible films and coatings, and the current state-of-the-art coating compositions. The most common edible barrier materials, in the category of those which would not be readily apparent to the consumer, include polysaccharides, e.g., alginate, pectin, carrageenan, starch, starch hydrolysates and cellulose derivatives; lipids, e.g., acetylated monoglycerides, natural waxes and surfactants; and proteins, e.g., gelatin, casein, serum albumin, ovalbumin, wheat gluten and zein, plus combinations of these. Another common edible barrier not encompassed in the above catagories is shellac. Films containing wheat gluten, which contains the wheat prolamine gliadin, and films containing zein have only received limited attention as edible coatings. Of the protein-based films, zein films have been found to possess relatively good water-barrier properties. Guilbert, "Technology and Application of Edible Protective Films," *In: Food Packaging and Preservation. Theory and Practice*, M. Mathiouthi (Ed)., Elsevier Applied Science Publishing Co., London, England, (1986), pp. 371-391.

Prolamines are characterized by their solubility in aqueous alcohol mixtures, or in aqueous mixtures of extreme pH (less than pH 2 or greater than pH 10) and therefore, most of the applications of prolamine films are from solutions of prolamines in alcohol and other solvent mixtures or water-based solutions having extreme pH's. The disadvantage of these coating systems in foods, hence the reluctance by the food industry for use of prolamine film systems, is that the solvents and/or pH levels are often incompatible with and difficult to remove from the food. Also, the use of organic solvents poses safety issues with the emission of vapors during the curing of the films, with the fire hazard that they pose, and with the possible residuals they may leave in the food.

Non-edible films based on prolamines have been described. Hansen (U.S. Pat. No. 2,047,961) describes a non-edible prolamine-based film which is formed by reacting the protein in an aqueous-alcoholic solution with formaldehyde and mixing the resultant with an alcohol soluble phenol-formaldehyde-type resin and a plasticizer. In U.S. Pat. Nos. 2,115,716 and 2,115,716, Hansen describes modifications to the solvent-based film systems in which he incorporates a plasticizing system comprised of amino acid esters to enhance the moisture resistance of the films and a high boiling (greater than 120° C.) organic solvent which balances the evaporation rates of the more volatile components in the coating mixture. Veatch (U.S. Pat. No. 2,134,769) describes improving the water resistance of non-edible zein films by the addition of waxes to alcoholic zein coating compositions, but required the addition of benzene and/or toluene to dissolve the waxes. Veatch (U.S. Pat. No. 2,194,337) also describes a non-edible zein film with improved grease resistance by incorporating urea and glycol in the alcohol mixture prior to casting the film. In U.S. Pat. No. 2,229,028 Sturken uses zein in an alcohol based coating composition with formaldehyde, and cures the films on paper sheets by the simultaneous application of heat and pressure. In U.S. Pat. No. 2,250,041 Sturken further describes a non-aqueous zein coating composition with improved plasticizers. In U.S. Pat. No. 2,311,485 Sturken introduces the use of sorbitol and triethanolamine as plasticizers for non-edible zein films deposited by evaporation from an ethanol solution. Evans and Manley (U.S. Pat. No. 2,437,8946) report that lactamides are excellent plasticizers for prolamine films, and that these may be hardened by reaction with an aldehyde. In U.S. Pat. No. 2,285,758 Sturken discloses a process for treating a zein film to give it water resistance. In this process, a zein film is brought into direct contact with steam.

Solvent-based coating compositions containing zein in solution with relatively large amounts of water have a tendency to gel on standing. Coleman (U.S. Pat. No. 2,185,123) describes a stable solution of zein in 95% alcohol to which an auxiliary solvent which is a lacquer solvent or a lacquer plasticizer, has been added. In U.S. Pat. No. 2,185,124 Coleman further describes a substantially non-aqueous coating composition which resists gelation, wherein zein is dissolved in alcohol containing not more than 5% water. Evans and Manley ("Stabilizing Zein Dispersions Against Gelation," *Industrial and Engineering Chemistry*, 1943, 35(2):230-232) and Evans (U.S. Pat. No. 2,402,128) stabilized the solvent solutions against gelation by using a heat treatment and reaction with aldehydes.

In U.S. Pat. No. 2,143,023, Meigs describes a derivatization of zein in which the zein is reacted together with formaldehyde and a secondary dialkylamine having less than nine carbon atoms. The zein derivative is soluble in dilute aqueous acids and may be used in non-edible coating compositions. In U.S. Pat. No. 2,377,237 James uses surfactants to disperse the zein in a predominantly aqueous phase.

Solvent-based prolamine films and coatings have been described for edible applications. In U.S. Pat. No. 2,791,509 Cosler discloses the use of zein as a surface coating for confectioneries. In these films, zein and an acetylated glyceride plasticizer are dissolved in a mutual organic solvent, preferably ethanol. The solution is deposited on the confectionery surface and the film is set by evaporation of the solvent. In U.S. Pat. No. 3,653,925 Anker, Foster and Loader disclose a coating formulation for foods comprised of wheat gluten, and optionally zein or soy protein isolate, dispersed in an alkaline, aqueous alcohol and plasticized with glycerol.

In food applications, several protein films such as gelatin, casein and zein, have been shown to have good water and/or lipid barrier properties. For example, zein provides a glossy surface possessing both good lipid and moisture barrier protection. The use of zein has been limited to the nut and confection industry, however, due to the need for organic solvents and/or extreme pH's.

SUMMARY OF THE INVENTION

The present invention relates to a method for coating a substrate with a prolamine film by applying a water-based prolamine latex which is substantially free of organic solvent to the substrate, which forms an edible coating or barrier on the substate. The water-based prolamine latex forms a continuous durable film when deposited on a surface and dried. The properties of the coating or barrier can be modified with various additives to the latex, e.g., to increase its flexibility or barrier properties.

Edible coatings produced by the present method are clear films which are non-toxic since they are formed from a naturally-occurring, common food protein. The present water-borne prolamine latex does not contain organic solvents or require extreme pH's, thus, the residues of these undesirable elements are minimized or eliminated. The prolamine films have excellent resistance to moisture, lipid and gas permeation.

DETAILED DESCRIPTION OF THE INVENTION

Figure 1:
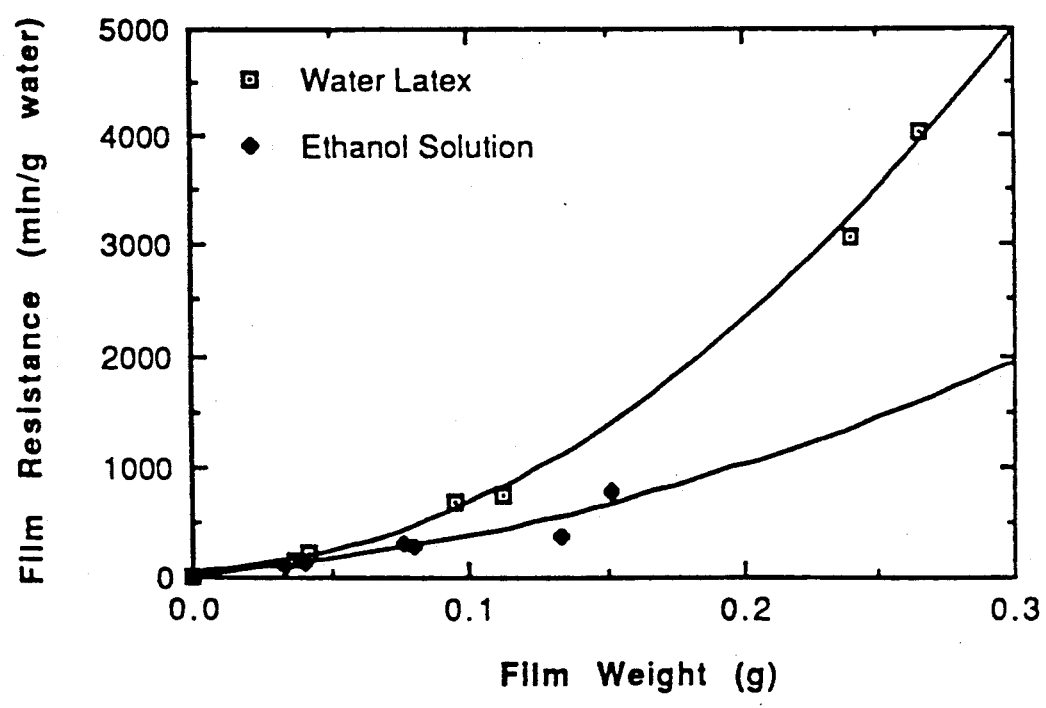
FIG. 1 is a graph illustrating the resistance of zein films measured at a transmembrane water vapor pressure of 0.79 psi and for a film area of 31 cm$^2$.

The present invention relates to a method of forming an edible barrier using an aqueous protein latex containing a prolamine suspended in an aqueous medium which is substantially free of organic solvent. The term "latex" as used herein means a suspension of water-insoluble particles having a median volume diameter of about 150 microns or less in an aqueous medium. The term "aqueous medium" refers to water or a water-based solution which contains at least 60% by weight water.

The prolamine latices used in the present method can be made by dissolving the prolamine in a solvent, such as ethanol, and combining the prolamine solution with an aqueous medium under mixing conditions. Prolamines are not soluble in the water-rich mixture, and precipitate, thereby forming a latex. Prolamine latices and methods for making them are described in detail in co-pending U.S. patent application Ser. No. 07/403,111 by Stark and Gross, filed Sep. 1, 1989, the teachings of which are incorporated herein by reference. The resulting latex can then be treated, e.g., by evaporation or diafiltration, to reduce the amount of prolamine solvent. The prolamine latex is substantially free of organic solvent, that is, contains none or only trace amounts (e.g., less than 1% by weight) of organic solvent. When the latex is applied to a substrate of choice and the water is evaporated, a continuous prolamine film forms.

Another method of forming the aqueous prolamine latex is to mill the prolamine to a fine particle size (e.g., less than about 50 microns) and to disperse them in an aqueous medium using a high-shear mixer. In this method, prolamine particles having an average particle size of less than about 15 microns are preferred.

Prolamines are characterized by their insolubility in water and solubility in aqueous alcohol (e.g., aqueous solutions of alcohol containing at least 40% alcohol), and by the presence in the protein of large amounts of hydrophobic amino acids, such as proline, glutamine and asparagine. The unusual solubility characteristics of prolamines is based on the fact that they are usually deficient in polar amino acids.

Prolamines are found in high concentrations in various grains, such as corn, wheat, barley, rice and sorghum, and in other plants and animal sources. Representative prolamine include, for example, zein, hordein, gliadin and kafirin.

The preferred prolamine for use in the present method is the alcohol-soluble protein-fraction of corn (*Zea mays*), named zein. The potential yield of zein is about one pound per bushel of corn. Zein can be readily obtained from corn gluten, which is a by-product of the corn wet milling industry. Both commercially available grades, with associated impurities, and purified forms of zein can be used.

The concentration of prolamine particles in suspensions made by the precipitation process described is generally up to about 5% by weight. The suspension may be further concentrated to up to about 40% by weight, by ultrafiltration, evaporation or other appropriate technique, or reduced to a dry powder, using standard techniques such as flash drying, lyophilization or spray drying. For example, ultrafiltration using membranes having a cut-off of 300,000 NMWL (nominal molecular weight limit) or less is a preferred method of concentrating the suspension and, at the same time, removing low molecular weight compounds dissolved in the aqueous medium. The concentrated protein can be diafiltered to reduce the amount of residual prolamine solvent to trace amounts. The diafiltration can be done continuously by staged addition of water or in a batch mode by constant volume batch diafiltration.

The concentrated suspension can, optionally, be dried to a powder. This can be accomplished by placing the suspension in a lyophilizer at an appropriate temperature (e.g., room temperature), at a pressure of less than about 100 millitorr (mtorr) until the water and other volatiles have been evaporated (to about 1–10% moisture content), and a fine powder remains. Alternative forms of drying, such as flash drying, fluid-bed drying, spray drying or vacuum drying can be used. This powder can then be stored and handled without refrigeration or other special handling procedures. Rehydration can be accomplished by adding the powder to water, or an aqueous medium, with agitation sufficient to resuspend the protein particles and form a suspension. The ratio of powder to water will depend upon the concentration of the final reconstituted product which is desired. For use as a coating or barrier, a suspension having a protein:water ratio of about 0.10 to about 0.25 by weight is preferred.

As an alternative to forming the latex via precipitation of the prolamine, a suspension of prolamine in a predominantly aqueous medium can be made by milling the protein and mechanically dispersing it in the aqueous medium. The protein may be milled to a fine particle size of preferably less than about 150 microns, and more preferably less than about 50 microns in an appropriate apparatus, e.g., a pin mill, or fluid energy mill optionally using a particle size classification device, such as a cyclone separator, to isolate the ultrafine particles. The milled protein may be suspended in the aqueous medium in a manner similar to the rehydration of the dehydrated latex precipitation product described above. The suspension may be made by adding the milled protein to water, or an aqueous medium, with agitation sufficient to individualize and suspend the particles. The ratio of protein to water will depend upon the concentration of the final reconstituted product which is desired. Additives in the aqueous medium may be used to enhance the properties of the suspension, and/or the resultant film.

The properties of the suspension can be modified for a given application, for example, by chemically and/or enzymatically altering the starting protein prior to precipitation or milling. Such modifications can produce a coating having enhanced barrier properties or mechanical stability. The functionality, surface properties and molecular weight distribution of the protein can be modified by hydrolysis with proteases, such as papain or chymotrypsin, to yield peptides having similar solubility characteristics as the untreated protein. Enzymatic hydrolysis can be carried out prior to making the suspension. The degree of hydrolysis can be controlled by varying the amount of enzyme used, the temperature of the reaction mixture or the reaction time during which the protein is exposed to the enzyme. Enzymatic hydrolysis of zein in 90% ethanol using a protease (e.g., papain or chymotrypsin) yielded polypeptides with a molecular weight of about 1,000 daltons. Unmodified zein has a dimer molecular weight of about 38,000 daltons. More importantly, the hydrolysate retains the solubility characteristics of the protein, i.e., the polypeptides are still insoluble in water but soluble in aqueous alcohol having at least 60% alcohol.

The properties of the product can be influenced by chemical modification of the proteins. Such modifications can include, for example, treating the proteins with an acid, base or other agent which alters the structure of one or more of the amino acid side chains, which, in turn, alters the character of the protein. For example, the high glutamine and asparagine content of prolamines, particularly zein, provides a means for manipulating the charge characteristics of the protein by deamidation, thereby providing a wide range of hydrophobicity. The preferred deamidation method involves mild acid-catalyzed deamidation (at a pH of about 1) at elevated temperatures (e.g., 25°-65° C.) for a period of time sufficient to accomplish the desired level of deamidation. The deamidation process may be followed by measuring the release of ammonia with an ammonia electrode. Deamidation is controllable, and may be terminated by the addition of ammonium carbonate or other base. Other examples of chemical modification include esterification of the protein with fatty alcohols, or acylation of the protein with fatty anhydrides.

Additives can be used to enhance certain properties of the films. For example, waxes (e.g., beeswax, carnauba wax, or paraffin wax), oils and/or surfactants e.g., acetylated glycerides, or diacetyl tartaric acid esters of mono- and di-glycerides (DATEM esters)) can be incorporated to improve the water resistance, and glycerol, or polyethylene glycols can be used to plasticize the film. Composite film structures with complex properties can be formed by using other polymeric or film-forming additives, such as other proteins (e.g., gelatin or casein), hydrocolloids (e.g., gum arabic, carrageenan or xanthan) or synthetic polymers (e.g., polyethylene glycol). Flavors, colors, anti-oxidants and/or preservatives can also add useful function to the films. Additives which are soluble in water can be incorporated in the coating formulation by direct dissolution in the aqueous medium of the latex. Additives which are insoluble in water may be dispersed by surfactants and added as an emulsion or latex, or incorporated in the zein microparticles during the precipitation process.

Water insoluble additives can be incorporated in the microparticles by dissolving or dispersing the additive in the alcoholic prolamine solution prior to the precipitation process in which the latex is formed. The additive, when incorporated in the prolamine microspheres, can be either evenly distributed throughout the sphere, in the center of the sphere or on the surface of the sphere, depending on the chemical nature of the additive. Alternatively, the additive may form microspheres or droplets separate from the protein microspheres.

The properties of the prolamine can be enhanced by crosslinking the prolamine prior to forming the latex by the addition of an enzyme which catalyzes intra- and/or intermolecular crosslinking of the protein, such as transglutaminase, or protein disulfide isomerase. Transglutaminase and protein disulfide isomerase cause inter- and intramolecular crosslinking of the protein through glutamine and cysteine, respectively. Transglutaminase catalyzes an acyl transfer reaction, in which the amide group of the amino acid glutamine is the acyl donor.

The present prolamine based suspensions can be used in various applications in the food and pharmaceutical industries, including as edible coatings or barriers in foods or for drugs, e.g., for tablets, such as aspirin. For these purposes, the coating should impart neither significant flavor nor color, so that it does not substantially alter the flavor or appearance of the food or the drug product. Some commercial preparations of prolamines may impart a yellow color to the protein suspension or may have an objectionable odor and/or flavor. To eliminate this problem, the proteins may be decolorized and/or deflavored. Decolorizing can be done prior to making the suspension. Decolorizing can be accomplished by known techniques for removing selected substances, such as extraction with organic solvents (e.g., acetone, hexane or methanol). Decolorizing can also be effected by passing the protein feed solution through a column, or other appropriate container, packed with an adsorbent, such as activated charcoal or a polymeric resin. For this purpose, non-polar, neutral, macroporous polymeric beads having a high surface area (e.g. from about 100 to about 1000 square meters per gram) can be used. Macroporous polystyrene or styrene-divinylbenzene copolymer beads having a pore size from about 10 to about 200 angstroms, are preferred. In one embodiment, the prolamine is dissolved in alcohol at a concentration of about 2 to about 40% and run through a column containing polystyrene beads at a space velocity of 2 l/hr per gm of beads. This procedure removes the color from the protein and passes the protein with a recovery of over 95%.

Deflavoring the protein removes the "grassy" or "grainy" flavor and/or odor which may be present in some proteins. One deflavoring method is to extract the dried protein with solvents such as ethanol, methanol, acetone, hexane or mixtures thereof. The solvent can then be removed from the prolamine by filtration and drying. Deflavoring can also can be accomplished by ultrafiltration. For this purpose, membranes having a pore size less than about 30,000 NMWL can be used. In one embodiment, the protein suspension is deflavored by filtering the suspension through a 30,000 NMWL hollow fiber filter cartridge. Protein microparticles treated with ultrafiltration exhibited reduced odor and flavor.

The edible coating or barrier can be applied to the substrate of choice by any suitable method, e.g., dipping, spraying, brushing, etc. The prolamine latex is applied to the substrate and dried under moderate heat to evaporate the water, and cause the microparticles to fuse or coalesce into a continuous film. Quickly raising the temperature of the film composition to above about 75° C. has the effect of driving off the water and of causing the protein microparticles to flow and fuse into a continuous, transparent film. Heat is applied to the surface, preferably via a radiant source, such as a high intensity lamp establishing a surface temperature of about 75° C. or above. For baked goods, the film may be cured directly in the baking process. For dry goods, the film may also be cured by high temperature bulk heating of the food or by application to a hot substrate. The important feature of the curing process is to drive off the moisture at a sufficiently high temperature to allow the protein microparticles to flow into a continuous film while there is enough moisture remaining in the film to allow for plastic flow. If a zein dispersion were to be dried at a low temperature, e.g., room temperature, and then subjected to heat, establishing a surface tempertaure of about 100° C., a continuous, transparent film would not form.

The present method using a water-based prolamine latex has several advantages: the latex can be dried to form a stable dry product which can be readily reconstituted with water, or other aqueous medium, prior to use. The prolamine latex is stable under conditions of mild pH (e.g., about 2 to about 10). The preferred pH range for food applications is from about pH 5 to about pH 7. The latex forms a continuous, durable film upon curing which is colorless, odorless, bland to the taste and non-toxic. The film can be applied to foods to form an edible barrier to moisture, lipid, gases, and/or other additives, such as colors, flavors, antioxidants and/or preservatives. The edible coating is particularly useful in prepared foods which are stored for a period of time prior to use. For example, frozen pizza presents many problems to the manufacturer. Different components of the product, such as pizza crust, tomato sauce, cheeses and toppings must be discretely maintained under storage conditions. Tomato sauce in particular must be kept from seeping into the crust rendering it soggy, and kept from imparting unwanted color to the cheeses and other toppings. Coating the crust with the present protein coating prior to applying the tomato sauce puts an effective barrier between these phases. Likewise, the present prolamine coating can be used in other food systems where it is desirable prevent migration of components such as keeping moisture from escaping or migrating within the systems, or preventing colors and/or flavors from blending. In drug applications, a prolamine coating can be applied to tablets for oral ingestion, for example, to provide a barrier between the drug and air or moisture.

The present film properties of the prolamine coating can be modified by controlling the concentration of prolamine in the latex, the mode of application and the number of layers applied. For example, where a thicker coating is desired, either a latex having a higher prolamine concentration or multiple layers can be applied.

The film formed from the present prolamine latex is superior to solvent-cast prolamine films. For example, analysis by scanning electron microscope (SEM) demonstrated that the water-borne zein coating was more dense and continuous than a zein film cast from ethanol. Without wishing to be bound by theory, it is believed that the water-borne protein films produced by the present method tend to stay on the surface of the substrate during curing, whereas solvent-borne systems tend to penetrate into the substrate. Therefore, most of the water-borne prolamine particles participate in forming the continuous film, in contrast to alcohol-based films which penetrate into the surface, thereby forming a more porous three-dimensional film structure.

The invention is further illustrated by the following examples.

EXAMPLES

Example A

Preparation of the Zein Latex

Commercially available zein was purified by extraction with acetone. An 800 g portion of dry zein (regular grade, F-4000; Freeman Industries, Inc., Tuckahoe, N.Y.) which had been milled to less than 150 microns in a MICRONIZER, fluid energy mill (Sturtevant, Inc., Boston, Mass.) was blended with 2 liters of dry acetone at about 45° C. for about 15 minutes. This slurry was then filtered in a coarse sintered glass funnel. The dry solids were resuspended in an additional 2 liters of dry acetone and extracted in a similar manner. A total of 6 extraction steps were made. The filtered solids were then placed in a tray and allowed to air dry overnight, yielding about 780 g of the purified material.

A zein solution was prepared by dissolving 630 g of the purified zein, 4.96 g soybean oil (CRISCO Brand, The Procter and Gamble Company, Cincinnati, Ohio) and 2.12 g of a DATEM ester (MYVATEM 30, Kodak Company, Rochester, N.Y.) in 9 liters of 90% ethanol (8.1 liters ethanol, 200 proof, and 0.9 liters water). This solution was heated to about 50° C. Another solution was prepared which contained 35 g medium viscosity carboxymethyl cellulose (Sigma Chemical Co., St. Louis, Mo.) and 35 g gum arabic (TIC Gums, Inc., Belcamp, Md.) in 36 liters of water. This solution was also heated to about 50° C.

The two solutions were combined in a flow through mixing apparatus. The mixing chamber was 65 mm in diameter by 27 mm long. The chamber was mechanically agitated via a 50 mm, 6-bladed turbine rotating at 500 rpm. The two solutions were pumped into the cell, with the aqueous solution being introduced at the base of the cell, and the ethanolic zein solution being introduced through a 0.125 inch, TEFLON ® tube, located near the tip of the impeller. The pumping rate allowed for an approximate residence time in the mixing apparatus of about 20 seconds. A precipitated zein latex was formed and removed by displacement at the top of the cell. The resulting suspension was comprised of particles with a median volume diameter of 0.93 microns (80% of the particles were between 0.38 and 2.38 microns) as measured on a MICROTRAC Small Particle Analyzer (Leeds & Northrup Instruments, North Wales, Penna.).

The zein latex was concentrated by ultrafiltration in a 5 ft² PELLICON System (Millipore, Inc., Bedford. Mass.) using an open channel configuration and regenerated cellulose membranes with a pore size of 300,000 NMWL. The latex was concentrated to approximately 18 liters, at which point it was diafiltered (constant volume filtration) with about 72 liters of water, to reduce the ethanol content. The latex was finally concentrated to about 9.5 liters (approximately 7% solids). The concentrate was then loaded into trays in an approximately 1 cm thick layer, and frozen at −70° C. The latex was freeze-dried in a VIRTIS shelf drier (Model 10-MR-TR, The Virtis Company, Gardiner, N.Y.) operating at conditions of about 60–100 millitorr vacuum, 40° C. platen temperature, and −80° C. condenser temperature.

Example B

Coating and Curing Method

The zein latex was coated onto glass slides and cured into a film using radiant heat. The freeze-dried latex prepared in Example A was rehydrated by adding the appropriate amount of cold water to the dry powder and homogenizing the mixture, over an ice bath, using a POLYTRON homogenizer (Brinkmann Instruments Co., Westbury, N.Y.) until the mixture was smooth. The zein latex was reconstituted to three different concentrations, as outlined in Table 1.

TABLE 1

| | Latex Compositions | | |
|---|---|---|---|
| Latex | Weight Dry Latex (g) | Volume of Water (ml) | Homogenization Time (min.) |
| I | 5.0 | 95 | 1 |
| II | 10.0 | 90 | 2 |
| III | 15.0 | 85 | 3 |

Glass microscope slides (Gold Seal, Becton Dickinson and Company, Lincoln Park, N.Y.) were coated by flowing the latex onto one side of the slide, and allowing the excess to freely drain off. The slides were placed on a TEFLON ® sheet and cured under a heat lamp (infrared, 250 W, General Electric Co., Fairfield, Conn.) located about 17 cm above the films for 15 minutes. The heat lamp gave a curing temperature of approximately 100° C. The film coatings were uniform, and essentially clear. The film formed from latex III included some bubbles due to the viscous nature of the latex and the formation of bubbles in the latex during homogenization.

Example C

Film Formation on a Porous Medium

Zein films were formed on filter paper from the reconstituted latices described in Example B. Filter disks (type 2, 4.25 cm, Whatman International Ltd., Maidstone, England) were coated by dipping in the latex, and allowing the excess to freely drain off. The disks were placed on a TEFLON ® sheet and cured under the heat lamp, located 17 cm above the film for 15 minutes. The heat lamp gave a curing temperature of about 100° C. The coatings were uniform, and the amount of zein incorporated in the films was essentially linearly related to the concentration of the latex solution in which the filters were dipped.

Example D

Permeability Measurement of the Zein Films

The permeability of zein films formed from the water-based latices were compared with the permeabilities of similar films formed from solutions of zein dissolved in alcohol. Ethanolic solutions of zein were prepared by dissolving 5.02, 10.00 and 15.01 g of zein (regular grade, F-4000 Freeman Industries, Inc., Tuckahoe, N.Y.) in 95, 90 and 85 ml, respectively, of 75% (v/v) ethanol. Films formed from these ethanol solutions were compared with films formed from the latices described in Example B. Films were formed on 7.0 cm WHATMAN No. 40 filter paper by dipping for 2 minutes, draining and curing under the heat lamp, located 17 cm above the film, for 10 minutes. Control films were prepared by treating filter paper with water or with 75% ethanol. An untreated filter paper control was also tested.

The film permeabilities were measured using a modified ASTM procedure. Approximately 20–25 g of 9 mesh anhydrous calcium sulfate ($CaSO_4$) dessicant (W. A. Hammond Drierite Company, Xenia, Ohio) was placed in a 63×17.5 mm aluminum weighting pan (Fisher Scientific Co., Pittsburgh, Pa.). Test films were sealed onto the pans with molten beeswax (Aldrich Chemical Company, Inc., Milwaukee, Wis.). These test packages were then stored in a desiccator maintained at a relative humidity of 75% (over a saturated NaCl solution), and at about 38° C., maintaining a 0.79 psi transmembrane differential water vapor pressure. Moisture uptake was determined gravimetrically. Each film type was tested in duplicate.

The zein films formed from the latex were more effective barriers to moisture than their comparable films formed from an ethanol zein solution. The enhancement of the filter paper barrier properties is due solely to the presence of the zein, since there was no observed difference between the three controls run. Correcting the observed film resistances for the presence of the filter paper, the permeability test results are shown in FIG. 1.

Example E

Permeability Measurement of Zein Films

The permeabilities of the zein films were measured in a manner similar to that described in Example D, however the packages were stored at 32% relative humidity rather than at 75%, maintaining a 0.34 psi transmembrane differential water vapor pressure. This test describes the effects of moisture level on the barrier properties of the zein film.

A series of films was made as described in Example D. In addition to the films described in Example D, a film was formed from milled zein. Zein (regular grade, F-4000) was milled in a MICRONIZER fluid energy mill to median volume particle diameter of 29 microns. A 15% (w/w) milled zein dispersion in water was prepared into which the filter paper was dipped and the film was cured as described in Example D. The films were used to seal aluminum weighing pans containing dessicant, as described in Example D, however these pans contained 35–36 g of dessicant. The packages were stored at approximately 38° C. over a saturated solution of magnesium chloride ($MgCl_2$), which creates a 32% relative humidity. The water flux through the films was monitored gravimetrically. Each film type was tested in duplicate.

Figure 2:
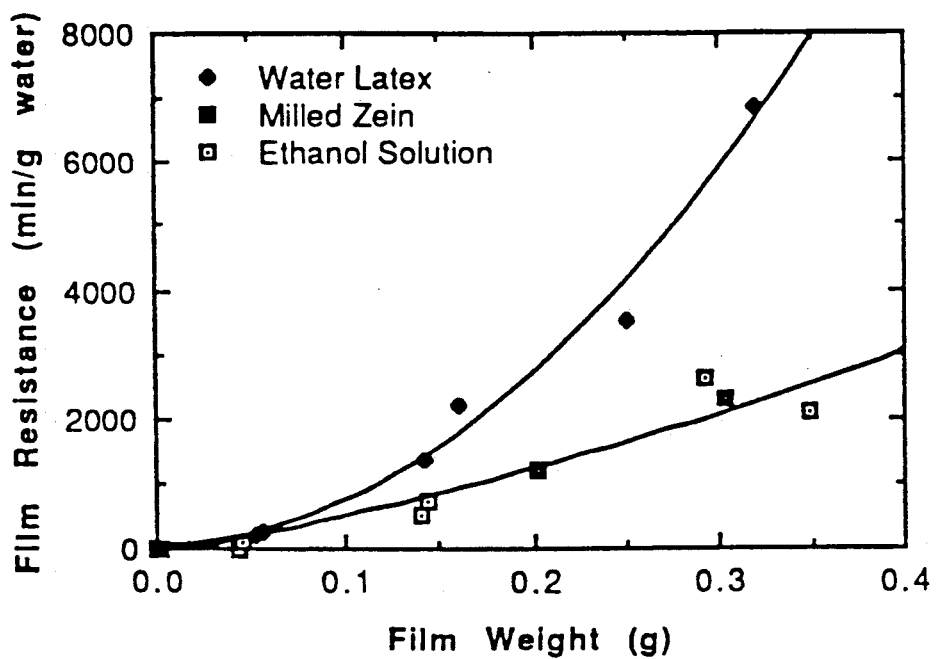
FIG. 2 is a graph illustrating the resistance of zein films measured at a transmembrane water vapor pressure of 0.34 psi and for a film area of 31 cm$^2$.

The film resistances were calculated by subtracting out the effect of the appropriate control barrier and quantifying the additional moisture barrier properties observed due to the presence of the zein film. None of the controls varied from one another, i.e., water and alcohol treatment had no effect on the barrier properties of the untreated filter paper. The results are given in FIG. 2, and show that the latex-based films give superior performance over the solution-based films. The milled zein also forms an effective barrier with performance similar to the solution-based film. The high external relative humidity used in Example D had little or no effect on the resistance of the film (when corrected for the driving force across the membrane, i.e., the differential water vapor pressure) when compared to the results of Example E. This reveals a relatively low sensitivity of the zein films to moisture. There is no significant difference in this effect when comparing the zein latex film with the conventional solution based zein film.

Example F

Barrier Properties of the Zein Latex in a Food System

The barrier properties of the latex, milled dispersion, and solution based zein films were quantified in a food system. The 15% solid latex formulation described in Example B, the 15% zein solution described in Example D, and the 15% solid dispersion of milled zein described in Example E were used to coat UNSALTED TOPS PREMIUM CRACKERS (Nabisco Brands Inc., East Hanover, N.J.). Each coating formulation was painted onto the surface of the cracker using a soft round No. 7 artist's brush. The film was then cured for 10 minutes by placing the cracker under the infrared heat lamp set at 17 cm above the cracker surface. Untreated, water, and alcohol coated controls were run. Each sample was run in duplicate. After coating, the crackers were stored overnight at ambient temperature over dessicant.

The crackers were stored at about 38° C. and 75% relative humidity (over saturated NaCl), and the moisture uptake was measured gravimetrically. The initial water uptake rate was determined. The initial water uptake rates of the coated crackers were compared to the controls to establish the relative water uptake shown in Table 2. All of the coatings formulations were equivalently effective barriers with the milled zein dispersion in water being the most effective barrier.

TABLE 2

Effect of the Zein Film on the Initial Water Uptake Rate When Coated Onto a Cracker

| Coating System | Rel. Uptake Rate |
|---|---|
| Untreated | 100% |
| Zein Latex (15% solids) | 63 |
| Milled Zein (15% solids) | 41 |
| Ethanol Solution (15% solids) | 49 |

The Average Cracker Weights 2.86 g, and has 47 $cm^2$ of Surface Area

EQUIVALENTS

Those skilled in the art will recognize or be able to ascertain using no more than routine experimentation, many equivalents to the specific embodiments of the invention described specifically herein. Such equivalents are intended to be encompassed in the scope of the following claims.

We claim:

1. A method of providing a barrier to gases, water, water vapor or oil on a substrate by coating the surface of the substrate with an edible prolamine comprising applying to the substrate an aqueous prolamine latex consisting essentially of prolamine microparticles that have a median volume diameter of from about 0.10 microns to about 150 microns that are suspended in an aqueous medium to form an aqueous suspension which is substantially free of organic solvent, devoid of a dispersing agent and which has from about 5% by weight to about 40% by weight of prolamine microparticles that are insoluble in the aqueous medium, and drying the latex under conditions sufficient for the prolamine microparticles to fuse and form an edible continuous prolamine film on the surface of said substrate.

2. A method of claim 1 wherein the prolamine is selected from the group consisting of zein, hordein, kafirin and gliadin.

3. A method of claim 2 wherein the prolamine is zein.

4. A method of claim 1 wherein the structure of the prolamine is enzymatically modified before application of the latex to the substrate.

5. A method of claim 1 wherein the structure of the prolamine is chemically modified before application of the latex to the substrate.

6. A method of claim 1 wherein the prolamine latex has a prolamine concentration of from about 10% to about 25% by weight.

7. A method of claim 1 wherein the substrate is a food or a drug.

8. A method of claim 7 wherein the drug is in tablet form.

9. A method of providing a barrier to gases, water, water vapor or oil on a substrate by coating the surface of the substrate with an edible prolamine comprising:

a) applying to the substrate an aqueous prolamine latex consisting essentially of an additive and prolamine microparticles that have a median volume diameter of from about 0.10 microns to about 150 microns that are suspended in an aqueous medium to form an aqueous suspension which is substantially free of organic solvent, devoid of a dispersing agent and which has from about 5% by weight to about 40% by weight of prolamine microparticles that are insoluble in the aqueous medium; wherein the additive is selected from the group consisting of waxes, oils, glycerides, proteins, flavors, colors, preservatives, anti-oxidants, hydrocolloids, glycerol and synthetic polymers; and b) drying the latex under conditions sufficient for the prolamine microparticles to fuse and form an edible continuous prolamine film on the surface of said substrate.

10. A method of claim 9 wherein the additive is a wax selected from the group consisting of beeswax, carnauba wax and paraffin wax.

11. A method of claim 9 wherein the additive is a hydrocolloid selected from the group consisting of gum arabic, carrageenan and xanthan.

12. A method of claim 9 wherein the additive is a glyceride selected from the group consisting of acetylated glycerides and diacetyl tartaric acid esters of monoglycerides and diglycerides.

* * * * *